United States Patent [19]

Huang

[11] 4,350,825

[45] Sep. 21, 1982

[54] PROCESS FOR THE MANUFACTURE OF STYRENE

[75] Inventor: I-Der Huang, West Paterson, N.J.

[73] Assignee: Exxon Research & Engineering Co., Florham Park, N.J.

[21] Appl. No.: 156,067

[22] Filed: May 30, 1980

Related U.S. Application Data

[60] Division of Ser. No. 960,735, Nov. 15, 1978, abandoned, which is a continuation of Ser. No. 755,245, Dec. 29, 1976, abandoned, which is a continuation-in-part of Ser. No. 685,057, May 10, 1976, abandoned.

[51] Int. Cl.$^3$ .............................................. C07C 51/12
[52] U.S. Cl. .................................. 562/406; 560/254; 568/814; 585/440
[58] Field of Search ........................... 562/406, 241; 260/669 QB; 568/814; 585/440

[56] References Cited

U.S. PATENT DOCUMENTS

| | | | |
|---|---|---|---|
| 3,769,326 | 10/1973 | Paulik et al. | 562/406 |
| 3,928,429 | 12/1975 | El-Chahaur et al. | 562/406 |
| 4,128,572 | 12/1978 | Cassar et al. | |

FOREIGN PATENT DOCUMENTS

| | | | |
|---|---|---|---|
| 753756 | 1/1971 | Belgium | 562/406 |

Primary Examiner—Paul J. Killos
Attorney, Agent, or Firm—C. Leon Kim; Robert A. Maggio

[57] ABSTRACT

A method to synthesize styrene from toluene by: (a) oxidizing toluene to form oxygenated toluene derivatives; (b) carbonylating said oxygenated products in the presence of a carbonylation catalyst and preferably a halogen promoter to produce phenylacetic acid; (c) hydrogenating said phenylacetic acid to synthesize phenylethyl alcohol; and (d) dehydrating said phenylethyl alcohol to obtain a high yield of styrene. In a preferred embodiment, a two-step, three-phase separation process can be employed for the separation and recovery of the phenylacetic acid formed in step (b) from the carbonylation catalyst and the halogen promoter which may have been employed in the carbonylation step (b) mentioned above by first separating the carbonylation product mixture into a gas-phase mixture and a liquid-phase mixture containing the phenylacetic acid, the carbonylation catalyst and the promoter; and then crystallizing the phenylacetic acid contained in the liquid-phase mixture in order to separate and thereafter recover the crystallized phenylacetic acid from the remaining liquid-phase mixture containing the carbonylation catalyst and the promoter.

8 Claims, No Drawings

PROCESS FOR THE MANUFACTURE OF STYRENE

CROSS-REFERENCE TO RELATED APPLICATIONS

This application is a division of U.S. application Ser. No. 960,735, filed Nov. 15, 1978, (now abandoned) which is a continuation of U.S. application Ser. No. 755,245, filed Dec. 29, 1976 (now abandoned), which is a continuation-in-part of U.S. application Ser. No. 685,057 filed May 10, 1976 (now abandoned).

BACKGROUND OF THE INVENTION

1. Field of the Invention

The present invention relates to a novel four-step method for synthesizing styrene by employing toluene as the starting material. More particularly, it pertains to a new method of making styrene at a markedly reduced cost by: (a) oxidizing toluene to obtain predominantly benzyl acetate; (b) carbonylating said benzyl acetate with a gaseous mixture containing carbon monoxide to form phenylacetic acid; (c) hydrogenating said phenylacetic acid to form phenyl ethanol; and (4) dehydrating said phenyl ethanol to produce styrene.

2. Description of the Prior Art

The art is replete with various processes for the production of styrene, see, e.g., Y. C. Yew and T. H. Vanden Bosch, STYRENE (Supplement A; 1973). However, these various methods have centered around the basic concept of dehydrogenating ethyl benzene to form styrene as follows:

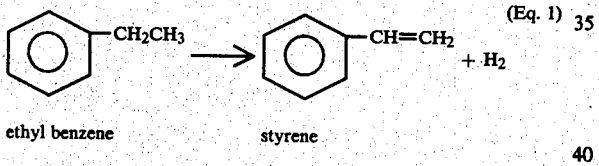

A variety of materials has been tried as starting materials in order to obtain ethyl benzene at a lower cost, which is used as the reactant in the conventional process described in Equation 1. Representative of them include benzene and its alkyl derivatives, toluene, vinylcyclohexene, ethyltoluene and 1,1-dimethylcyclohexane. None of the chemicals listed above, except benzene, has proven to be commercially feasable due to poor conversion rates and low yields. In view of the above, benzene and ethylene have been most commonly used to first prepare ethyl benzene and then manufacture styrene as follows:

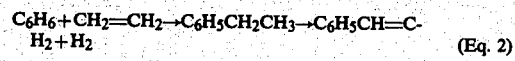

During the last decade or so, however, benzene and ethylene have experienced dramatic price increases. Accordingly, in view of the above, the need has existed for an effective commercial process for manufacturing styrene, which commands itself to a wide variety of commercial uses such as the manufacture of synthetic rubbers and various styrene-based plastics, at a lower manufacturing cost than conventional techniques known to the art.

SUMMARY OF THE INVENTION

It has now been discovered that, by taking a route entirely different from conventional methods such as the one described in Equation 1 or 2, styrene can be produced at a far less cost. In accordance with the instant invention, styrene is synthesized in four major steps as follows: (a) oxidizing toluene in the presence of an oxidation catalyst to form an oxygenated product containing benzyl acetate; (b) contacting the oxygenated product formed in step (a) with a gaseous mixture containing carbon monoxide in the presence of a carbonylation catalyst and preferably a halogen promoter to form phenylacetic acid; (c) hydrogenating the phenylacetic acid so produced in step (b) in the presence of a hydrogenation catalyst to form phenylethyl alcohol: and (d) dehydrating the phenylethyl alcohol formed in step (c) to produce styrene. This novel reaction scheme is further illustrated in the following equation:

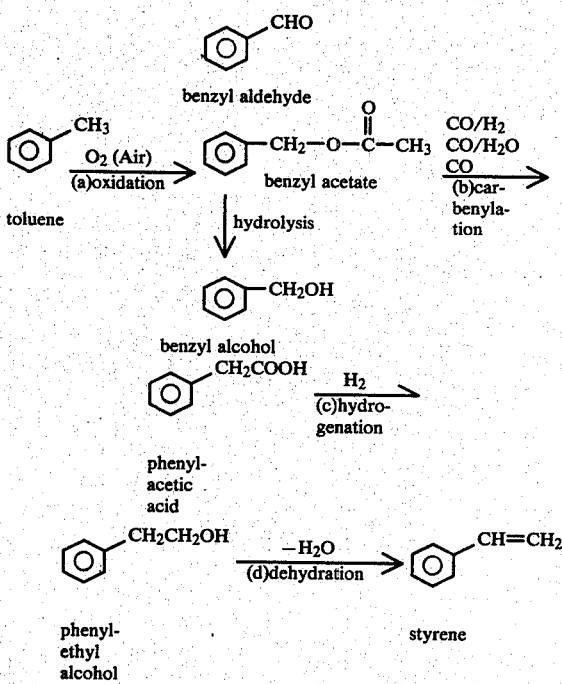

As the first major step, toluene is contacted with air, oxygen or other oxygen sources, and acetic or propionic acid, in either the liquid or the vapor phase, in the presence of an oxidation catalyst and preferably a promoter at a temperature ranging from about 50° to about 400° C., preferably from about 80° to about 300° C., and more preferably from about 100° to about 200° C. and at a pressure ranging from about 1 to about 50 atm., preferably from about 1 to about 30 atm., more preferably from about 1 to about 20 atm. to produce an oxygenated product containing about 0 to about 20 mole % benzyl aldehyde and about 80 to 100 mole % benzyl acetate or benzyl propionate with the overall conversion of about 50–100 mole % of toluene as follows:

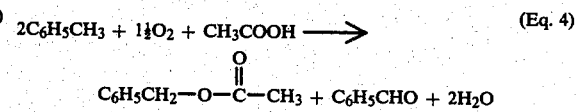

Variable-valent metals or compounds of variable-valent metals such as Tl, Te, Ce, Au, Bi, Pd, Sb, Mn, V, Ga, As, Co, Cu, Se, Cr or Ag may be employed either alone or in combination as the oxidation catalyst. Preferred catalysts are the organic and inorganic derivatives of Au, Bi, Tl, Ce, Se, Te and Pd. Specific examples of these preferred catalytic compounds are inorganic salts such as chlorides, bromides, iodides, sulfates and nitrates; and organic salts such as acetates and propionates of Au, Bi, Tl, Ce, Se, Te and Pd. These variable-valence metals or their mixtures may be beneficially supported, especially in the case of the vapor phase oxidation, on such materials as $SiO_2$, $Al_2O_3$, $TiO_2$, ZrO, MgO, active carbon, kieselguhr, charcoal and the like. As described in U.S. Pat. No. 3,399,956 (Hirose et al.; 1968), compounds of redox metals such as copper, mercury, chromium, manganese, iron, cobalt and nickel may be preferably employed, particularly in the case of the liquid phase oxidation, alone or together with a halogen ion such as fluoride, iodide, bromide or chloride in order to promote the catalytic effect of the variable-valent metallic salts. Non-limiting representative of such redox metallic derivatives include inorganic and organic salts, e.g., iodides, bromides, chlorides, oxides, nitrates, carbonates and sulfates, and acetates and propionates, of the metals listed above. In addition, halides of Groups IA and IIA metals may also be beneficially employed as effective promoters for the oxidation catalysts. These alkali metal and alkaline earth metal halides, e.g., chlorides, bromides, iodides and fluorides of Li, Na, K, Be, Mg, Sr, Ba and Ca, are known to increase the solubility of the variable-valent metallic salts in the reaction medium.

Optionally, the acetic or propionic acid consumed in the oxidation step represented by Equation 4 can be recovered by hydrolyzing benzyl acetate or benzyl propionate to form benzyl alcohol as follows:

$$C_6H_5CH_2OCOCH_3 + H_2O \rightarrow C_6H_5CH_2OH + CH_3COOH \quad \text{(Eq. 5)}$$

Acid catalysts which are commonly used in ester hydrolysis can be employed to obtain a 90% or higher yield of benzyl alcohol in the hydrolysis reaction represented by Equation 5. Among such acid catalysts are included sulfuric acid, hydrochloric acid, nitric acid, chloric acid, benzenesulfonic acid, p-toluenesulfonic acid and cation exchange resin. Sulfuric acid is most widely used. Reaction temperatures to be used in this hydrolysis of benzyl acetate range from about 50° to about 300° C., preferably from about 70° to 250° C., and more preferably from about 80° to about 200° C. In order to carry out the hydrolysis in the liquid phase at a given temperature, sufficient pressures, e.g., ranging from about 1 to about 30 atm., should be maintained. The hydrolysis of benzyl acetate makes it possible to recover acetic acid for reuse at the oxidation step, thereby reducing the reactor requirement in the ensuing carbonylation step.

As the second major step, benzyl aldehyde, benzyl acetate and/or benzyl alcohol derived from the oxidation of toluene as discussed above are then carbonylated to form phenylacetic acid in the liquid phase with carbon monoxide or a gaseous mixture of hydrogen and carbon monoxide or carbon monoxide with water as follows:

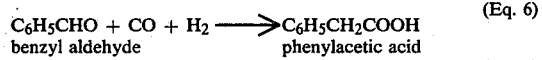
benzyl aldehyde     phenylacetic acid (Eq. 6)

benzyl alcohol (Eq. 7)

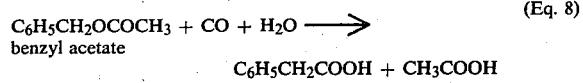
benzyl acetate (Eq. 8)

$$C_6H_5CH_2COOH + CH_3COOH$$

Widely-known Group VIII metal carbonylation catalysts, e.g., Co, Ni, Rh, Fe, Pd, Pt, Ir, may be employed with or without a halogen promoter such as iodine, bromine or chlorine. Rhodium or iridium catalyst promoted with the halogen ion is preferred. In addition, Group VIII metals complexed with Group VA compounds such as phosphine, arsenic and antimony may also be beneficially employed. Examples of such complexes may include the trialkylphosphites, the tricycloalkylphosphites, the triarylphosphites, the triarylphosphines, the triarylstibines, and the triarylarsines of, for example, rhodium. Acetic or propionic acid may be optionally employed to provide an acidic medium to facilitate the carbonylation. The volume ratio of $H_2$/CO mixture employed ranges from about 0/100 to aout 80/20, preferably from about 0/100 to about 70/30, more preferably from about 5/95 to about 65/35. This carbonylation can be carried out at a temperature ranging from about 100° to about 300° C., preferably from about 150° to about 250° C., and more preferably from about 150° to about 220° C.; and at a pressure ranging from about 10 to about 350 atm., preferably from about 30 to about 300 atm., and more preferably from about 30 to about 200 atm. A number of catalysts which are normally used in deriving carboxylic acids from alcohols can be employed in the instant carbonylation step. Illustrative of these catalysts include the rhodium and the iridium metals, and their inorganic and organic compounds such as bromides, iodides, chlorides, oxides, nitrates, carbonates, and phenyl compounds. While a more detailed list of the catalytic compounds can be found in, for example, U.S. Pat. No. 3,813,428 (Paulik et al.; 1974), specific compounds such as $RhBr_3$, $RhI_3$, $RhBr_3 \cdot H_2O$, $Rh_2O_3$, $Rh(NO_3)_3$, $IrCl_3 \cdot 3H_2O$, $IrO_2$ and the like can be beneficially employed. It is known that the catalytic effect of these rhodium or iridium compounds can be greatly enhanced by the presence of a halogen moiety, e.g., iodide, chloride or bromide. Such compounds as hydrogen halide, alkyl or aryl halide, metallic halide and the halides of ammonium, phosphonium, arsonium and stibonium can be employed as the source of the halogen promoter.

As the third major step toward the formation of styrene, phenylacetic acid synthesized from benzyl acetate, benzyl aldehyde and/or benzyl alcohol is then hydrogenated in the liquid phase to form phenyl ethanol as follows:

$$C_6H_5CH_2COOH + 2H_2 \rightarrow C_6H_5CH_2CH_2OH + H_2O \quad \text{(Eq. 9)}$$

This hydrogenation of phenylacetic acid can be conducted at temperatures between about 100° and 350° C., preferably between about 120° and about 330° C., and more preferably between about 130° and about 300° C., and at pressures between about 10 and about 400 atm., preferably between about 50 and 375 atm., and more preferably between about 100 and 350 atm. in the presence of a hydrogenation catalyst. A $C_1$-$C_{12}$ alkyl alcohol such as methanol, ethanol, propanol and butanol may be employed as a promoter/solvent. Group IIA metallic ions, e.g., $Ba^{+2}$, $Ca^{+2}$ and an ammonium radical may also be employed as a promoter. Catalysts amenable to the instant hydrogenation step include the compounds of Cu, Groups VIB and VIII metals such as Cr, Mo, W, Co, Ni and mixtures thereof. Non-limiting examples of these catalysts include sulfides and oxides of Cu, and Groups VIB and VIII metals, e.g., MoS, NiWS; copper oxide, chromium oxide, copper-chromium oxide; and cobalt-molybdenum and copper-chromium metallic mixtures. In general, support materials such as alumina, alumina modified with other metallic oxides such as magnesia, kieselguhr, pumice, carbon, charcoal and silica are preferably employed as the carrier of the metallic catalyst. Among the preferred supported catalysts are copper-chromium impregnated in an alumina-magnesia carrier, i.e., $Cu-Cr/Al_2O_3 \cdot MgO$ and molybdenum-sulfur on charcoal.

In connection with the carbonylation and the hydrogenation steps, publications made by U.S. Bureau of Mines, e.g., I. Wender et al., "Homologation of Alcohols," JACS, vol. 71 (1949), pp 4160–61, and another article by the same authors, entitled "Chemistry of the Oxo and Related Reactions. IV. Reductions in the Aromatic Series," appearing on pp. 4160–61 of JACS, vol. 71 (1951), suggest that phenylethyl alcohol may be synthesized by direct homologation of benzyl alcohol, i.e., addition of a methylene group to benzyl alcohol. The articles, however, indicate a low yield of phenylethyl alcohol, e.g., 26%. Accordingly, if the yield from the homologation can be sufficiently improved, e.g., above 50%, the second and the third steps described above may be alternatively replaced with a homologation step.

As the fourth and last major step of the overall process for the manufacture of styrene from toluene, phenyl ethanol which is synthesized by hydrogenating phenylacetic acid as shown in Equation 9 is then dehydrated in the liquid or optionally in the vapor phase at a temperature ranging from about 100° to about 400° C., preferably from about 150° C. to about 350° C., more preferably from about 180° to about 350° C. and at pressures between about 0.2 and 70 atm., preferably between about 1 and 35 atm., and more preferably between about 1 and about 20 atm., in order to produce styrene as follows:

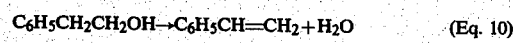

$$C_6H_5CH_2CH_2OH \rightarrow C_6H_5CH=CH_2 + H_2O \qquad (Eq. 10)$$

Although thermal, noncatalytic dehydrations are possible at elevated temperatures, improved results can be obtained by employing various dehydration catalysts known to the art. For example, metallic oxides such as titanium, thorium or aluminum oxide may be beneficially used. The dehydration of phenyl ethanol can also be carried out in an inert liquid medium in the presence of an acid and/or a so-called high-surface-area solid dehydration catalyst. Representative of preferred acid catalysts include a variety of mineral acids such as sulfuric acid, perchloric acid and phosphoric acid; carboxylic acids such as oxalic acid and salicyclic acid; and also such acids as p-toluene-sulphonic acid and other aryl sulphonic acids of benzene and its homologs. Suitable high-surface-area catalysts are activated carbon, natural clays, molecular sieves, silica-aluminas and activated aluminas. The term, high-surface-area catalyst, is, as defined in U.S. Pat. No. 3,526,674 (Becker et al.; 1970), used to mean a catalyst having a surface at least in excess of about 15 sq. meters per gram of the catalyst. A large number of organic materials can be employed to provide a suitable liquid reaction medium. Some of the suitable materials, as disclosed in the Becker patent, include high boiling hydrocarbons, high-boiling petroleum distillates, mineral oils and various high-boiling polar materials. One of the preferred solvents is the high-boiling residue formed during the dehydration reaction. In addition, it is also desirable to employ low-boiling organic compounds such as methanol, acetic acid, t-butyl alcohol and the like. The use of such low-boiling solvents is preferred since they tend to minimize the polymerization of styrene.

The present invention further provides an economic method of separating and recovering the phenylacetic acid formed at the carbonylation step from the carbonylation catalyst and the carbonylation promoter, i.e., a rhodium or iridium compound and a halogen promoter. This inventive embodiment not only makes it possible to obtain highly purified phenylacetic acid but also offers a surprisingly effective means of minimizing the loss of expensive catalyst metals, thereby making the entire process more economically feasible. In accordance with this inventive embodiment, the carbonylation product mixture containing the phenylacetic acid, the halogen promoter and the carbonylation catalyst is first sent to a separation chamber or a series of separation chambers in order to separate gaseous compounds, e.g., synthesis gas mixture and other low-boiling compounds, from liquid compounds, e.g., solvent, halogen promoter, rhodium or iridium compound and phenylacetic acid. The syn gas mixture recovered as the tops effluent from the separation chamber(s), which may contain traces of halogen moieties and solvent, is first scrubbed with the carbonylation feedstream containing benzyl acetate, benzyl aldehyde and/or benzyl alcohol; and is then recycled to the carbonylation reactor for reuse. The liquid-phase mixture, discharged as the bottoms effluent from the separation chamber(s), is then collected and chilled to the melting point or to a temperature slightly below the melting point of phenylacetic acid, e.g., about 75° C. at one atmospheric pressure, in order to crystallize the phenylacetic acid. This crystallization results in the following liquid-solid phase separation: the liquid phase containing the catalyst, the promoter and the solvent; and the solid phase containing mainly the phenyl-acetic acid. The crystalline product, if necessary, is then washed with a solvent, e.g., acetic or propionic acid, or a liquid mixture of the carbonylation reactants, e.g., benzyl acetate, benzyl aldehyde and/or benzyl alcohol, in order to remove rhodium or iridium moieties remaining in the crystalline substance. Further, if desired, the crystalline product may be remelted, recrystallized and washed in order to maximize the purity of the phenylacetic acid separated and also minimize the catalyst loss. The liquid mixture containing the catalyst and the solvent recovered from this liquid-solid phase separation step may be recycled to the carbonylation reactor for reuse. The crystalline phenylacetic acid so recovered may be then remelted or dissolved in a $C_1-C_{12}$ alkyl alcohol and hydrogenated in accordance with the instant invention.

DESCRIPTION OF THE PREFERRED EMBODIMENTS

The present invention may be further understood by reference to the following examples. Examples 1 and 3, being in the present tense, should be taken in conjunction with Examples 2 and 4 to 8, as the best mode of carrying out the instant invention, and not as reflecting an account of acts actually carried out by the applicant.

EXAMPLE 1

This example is intended to demonstrate that about 99% of reacted toluene can be converted in the liquid phase to the desired oxygenated toluene derivatives.

A one-liter flask is charged with 450 grams of acetic acid, 92 grams of toluene and a catalyst mixture containing 34.1 grams of 5 wt. % palladium on charcoal, 100 grams of KOAc and 14 grams of stannous acetate. While the flask containing the reaction mixture is constantly stirred at about 100° C., air is continuously blown through the reaction mixture at a rate of about 0.5 liter/min. measured at 25° C. and 760 mm Hg for about 9 hours. Gas chromatographic (G.C.) analysis of the reaction mixture shows that about 80 mol % of toluene is converted to form approximately 91.5 mol % of benzyl acetate, 7.5 mol % of benzyl aldehyde and 1 mol % of benzyl diacetate.

EXAMPLE 2

This example is designed to show that about 90 mole % of toluene reacted can be converted to benzyl acetate by carrying out the oxidation of toluene in the vapor phase.

A mixture of 70.7 wt. % acetic acid, 23.2 wt. % toluene and 6.1 wt. % water was first, at the rate of 0.198 gm./min., vaporized and then fed into a $\frac{3}{8}''$ I.D. stainless-steel tubular reactor packed with about 4.7 gm. of palladium on alumina support, at 160°–170° C. and about 30 psig. The palladium content contained in the supported catalyst was about 2% by weight. After about two hours of continuously running the reaction, the gaseous reaction product was directly sent to an on-line G.C. analyzer. The G.C. analysis showed that about 15% of toluene was converted; and that no product other than benzyl acetate was formed from the vapor phase reaction. A check based on the feed/product material balance indicated that the yield of benzyl acetate was over 90 mole % of toluene reacted.

EXAMPLE 3

This example is intended to show that about 90 mol % of benzyl alcohol derived from the oxidation of toluene can be converted to phenylacetic acid.

A batch autoclave is charged with 213 grams of acetic acid, 108 grams of benzyl alcohol, 0.428 grams of $RhCl_3.3H_2O$ and the promoter containing 57 wt. % of aqueous hydriodic acid (HI). The autoclave is pressurized with CO to 1,000 psig at 175° C. until the complete conversion of the benzyl alcohol charged takes place. G.C. analysis of the reactor content indicates that the selectivity to phenylacetic acid is about 90 mol %.

EXAMPLE 4

This example is designed to demonstrate that about 91 mol % of benzyl acetate can be hydroformylated to form desirable compounds, i.e., phenylacetic acid and dibenzyl ether. Dibenzyl ether so formed can be recycled to the carbonylation step.

An autoclave was introduced with 100 grams of benzyl acetate, 0.25 grams of aqueous rhodium oxide and 1 gram of iodine. The batch reactor was then pressurized with a syn gas mixture having the volume ratio of $H_2/CO=60/40$ to 1,000 psig at 150° C. The hydroformylation was continued at the constant pressure for about 3 hours. The final product was found to contain about 22 mol % of phenylacetic acid and about 69 mol % of dibenzyl ether which can be further carbonylated to form phenylacetic acid as shown in Example 5.

EXAMPLE 5

This example is designed to demonstrate that benzyl alcohol can be carbonylated by employing a synthesis gas to produce a high yield, e.g., about 90% based on benzyl alcohol charged, of phenylacetic acid; and that dibenzyl ether and benzylphenyl acetate may be formed as precursors to phenylacetic acid.

To the same autoclave employed in Example 4 were introduced 30 grams of benzyl alcohol, 0.1 gram of rhodium oxide and 0.3 gram of iodine. The autoclave was then pressurized with a synthesis gas mixture containing about 60 vol. % hydrogen and about 40 vol. % CO to about 1,000 psig. at about 125° C. for one hour. G.C. analysis of the reaction sample at the moment indicated that about 87.6 mol % of benzyl alcohol introduced was converted to: 11.1 mol % of phenylacetic acid, 26.5 mol % of dibenzyl ether, 58.1 mol % benzylphenyl acetate and 2.3 mol % of toluene. The carbonylation, under the same synthesis gas pressure and the temperature, i.e., 1,000 psig. and 125° C., was then continued for two additional hours. G.C. analysis of the three-hour reaction product showed that essentially all of the benzyl alcohol, dibenzyl ether and about 90% of the benzylphenyl acetate which had been detected in the one-hour reaction product were converted to phenylacetic acid, producing phenylacetic acid in a yield higher than 90% based on benzyl alcohol charged.

EXAMPLE 6

This example is designed to show that benzyl aldehyde can be hydroformylated to form phenylacetic acid.

To the same autoclave employed in Example 4 were introduced 30 grams of benzyl aldehyde, 0.1 gram of rhodium oxide and 0.3 gram of iodine. The autoclave was then pressurized with a synthesis gas mixture having the volume ratio of $H_2/CO=60/40$ to 1,000 psig and 150° C.; and was maintained at the operating conditions for about 3 hours. G.C. Analysis of the final product indicated that about 70 mol % of the benzyl aldehyde was converted to yield 73.3 mol % of phenylacetic acid, 7.1 mol % of toluene and 19.6 mol % of heavy-boiling product which was mainly dibenzyl ether.

EXAMPLE 7

This example is designed to show that a high yield, e.g., about 95.2 mol %, of phenyl ethanol can be obtained from the hydrogenation of phenylacetic acid.

A 50 c.c. volume batch reactor was charged with 20 grams of phenylacetic acid (0.147 mole), 30 grams of ethanol, and 5 grams of molybdenum-sulfur on charcoal as catalyst. This reactor was then pressurized with hydrogen to 3,000 psig at 300° C. for about 8 hours. G.C. analysis of the product showed that 17.1 grams (0.140 mole) of phenyl ethanol was formed. Other main product was identified as ethylbenzene; and the selectivity to phenyl ethanol was about 95.2 mol %.

EXAMPLE 8

Example 8 is designed to illustrate that styrene can be obtained in high yields by dehydrating phenylethyl alcohol.

Phenylethyl alcohol was introduced, at a rate of 1.38 gm./min., into a one-inch O.D. stainless-steel tubular reactor packed with 162 c.c. of aluminum catalyst (Alcoa H-151). The reactor, which was operated at 345° C., was also charged with nitrogen at the rate of about one standard cu. ft./hr. G.C. analysis of the dehydration product showed that over 98% of the phenyl ethanol introduced was converted to form: 94.0 mol % of styrene, 0.8 mol % of ethyl benzene and traces of toluene and diphenylethyl ether. Accordingly, the yield of styrene based on phenyl ethanol reacted was about 95.6%.

What is claimed is:

1. A process for the formation and recovery of phenyl acetic acid which comprises:
   (a) carbonylating at least one reactant selected from the group consisting of benzyl acetate, benzyl propionate, benzylaldehyde, and benzyl alcohol by contacting a liquid reaction mixture comprising at least one of said reactants with a carbon monoxide containing gas under conditions and in a manner sufficient to form liquid phenyl acetic acid, said liquid reaction mixture additionally comprising at least one homogeneous Group VIII element containing catalyst capable of catalyzing said carbonylation reaction, said Group VIII element being selected from the group consisting of Rh, Ir, and mixtures thereof, and at least one halogen containing promoter capable of promoting said catalyzed carbonylation reaction;
   (b) recovering said liquid reaction mixture resulting from step (a) containing liquid phenyl acetic acid and cooling said mixture to a temperature sufficient to crystalize said liquid phenyl acetic acid, thereby forming a two phase mixture having a solid phase and a liquid phase, said solid phase containing said crystalyzed phenylacetic acid and said liquid phase containing the remainder of said components in said liquid reaction mixture and sufficient carbonylation catalyst to catalyze the carbonylation reaction of step (a);
   (c) separating said liquid and solid phases; and
   (d) recycling said separated liquid phase back to liquid reaction mixture of step (a).

2. The process of claim 1 wherein the halogen promoter is selected from the group consisting of hydrogen halides, alkyl halides, aryl halides, ammonium halides, phosphonium halides, arsonium halides, stibonium halides, halogens, and mixtures thereof.

3. The process of claim 1 wherein the carbonylation catalyst is selected from the group consisting of rhodium metals, iridium metals, rhodium containing compounds, rhodium containing complexes, iridium containing compounds, iridium containing complexes, and mixtures thereof.

4. The process of claim 1 wherein said reaction medium of step (a) additionally contains at least one acid selected from the group consisting of acetic acid, and propionic acid.

5. A process for the manufacture of styrene which comprises:
   (1) oxidizing toluene in the presence of (i) at least one variable-valent metallic catalyst; (ii) at least one redox metallic promoter; (iii) at least one halogen ion; and (iv) acetic acid or propionic acid to form an oxygenated product containing at least one member selected from the group consisting of benzyl acetate and benzyl propionate;
   (2) carbonylating at least one of said oxygenated products of step 1 to form phenyl acetic acid by the steps comprising:
      (a) contacting a liquid reaction mixture comprising at least one of said oxygenated products with a carbon monoxide containing gas under conditions and in a manner sufficient to form liquid phenyl acetic acid, said liquid reaction mixture additionally comprising at least one homogeneous Group VIII element containing catalyst capable of catalyzing said carbonylation reaction, said Group VIII element being selected from the group consisting of Rh and Ir, and at least one halogen containing promoter capable of promoting said carbonylation reaction;
      (b) recovering said liquid reaction mixture resulting from step 2-a containing liquid phenyl acetic acid and cooling said mixture to a temperature sufficient to crystallize said liquid phenyl acetic acid, thereby forming a two phase mixture having a solid phase and a liquid phase, said solid phase containing the crystallized phenyl acetic acid and said liquid phase containing the remainder of said components in said liquid reaction mixture and sufficient carbonylation catalyst to catalyze the carbonylation reaction of step (a);
      (c) separating said liquid and solid phases and recovering crystallized phenyl acetic acid from the solid phase; and
      (d) recycling said separated liquid phase back to the liquid reaction mixture of step (2-a);
   (3) hydrogenating the phenyl acetic acid recovered from the solid phase resulting from step (2) in the presence of a hydrogenation catalyst to form phenylethyl alcohol;
   (4) dehydrating the phenylethyl alcohol of step (3) to form styrene.

6. The process of claim 5 wherein the halogen promoter is selected from the group consisting of hydrogen halides, alkyl halides, aryl halides, ammonium halides, phosphonium halides, arsonium halides, stibonium halides, halogens, and mixtures thereof.

7. The process of claim 5 wherein the carbonylation catalyst is selected from the group consisting of rhodium metals, iridium metals, rhodium containing compounds, rhodium containing complexes, iridium containing compounds, iridium containing complexes, and mixtures thereof.

8. The process of claim 5, wherein said reaction medium of step (2-a) additionally, contains at least one acid selected from the group consisting of acetic acid and propanoic acid.

* * * * *